United States Patent [19]

Ota

[11] Patent Number: 4,525,033
[45] Date of Patent: Jun. 25, 1985

[54] LIQUID CRYSTAL COMPOUND AND COMPOSITIONS CONTAINING SAME

[75] Inventor: Tadashi Ota, Suwa, Japan

[73] Assignee: Kabushiki Kaisha Suwa Seikosha, Tokyo, Japan

[21] Appl. No.: 328,155

[22] Filed: Dec. 7, 1981

Related U.S. Application Data

[63] Continuation of Ser. No. 46,583, Jun. 7, 1979, abandoned.

[30] Foreign Application Priority Data

Jun. 8, 1978 [JP] Japan ................... 53-69228
Jul. 7, 1978 [JP] Japan ................... 53-82798
Jul. 26, 1978 [JP] Japan ................... 53-89018

[51] Int. Cl.$^3$ ............................ G02F 1/13; C09K 3/34
[52] U.S. Cl. ............................ 350/350 R; 252/299.63;
260/465 D; 560/1; 350/333
[58] Field of Search .................. 260/465 D; 560/1;
252/299.63; 350/350 R, 332, 333

[56] References Cited

U.S. PATENT DOCUMENTS 4,149,413 4/1979 Gray et al. ................... 252/299
4,372,871 2/1983 Toriyama et al. ............ 252/299.61

FOREIGN PATENT DOCUMENTS

| | | | |
|---|---|---|---|
| 105701 | 5/1974 | German Democratic Rep. | 252/299.63 |
| 132591 | 10/1978 | German Democratic Rep. | 252/299.63 |
| 54-6884 | 1/1979 | Japan | 252/299.63 |
| 54-118389 | 9/1979 | Japan | 252/299.63 |
| 54-148184 | 11/1979 | Japan | 252/299.63 |
| 55-3451 | 1/1980 | Japan | 252/299.63 |
| 55-21417 | 2/1980 | Japan | 252/299.63 |
| 2017742 | 10/1979 | United Kingdom | 252/299.63 |
| 2028363 | 3/1980 | United Kingdom | 252/299.63 |

OTHER PUBLICATIONS

Demus, D., Nonemissive Electrooptic Displays, Kmetz, R. A. et al., Plenum Press, N.Y.-London, pp. 83–117 (1976).
Deutscher, H. J. et al., Z. Chem., vol. 17, p. 64 (1977).

*Primary Examiner*—Teddy S. Gron
*Attorney, Agent, or Firm*—Blum, Kaplan, Friedman, Silberman & Beran

[57] ABSTRACT

Liquid crystal compounds which are para-substituted phenyl esters of para-substituted cyclohexyl carboxylic acid, are effective in compositions for use in liquid crystal display devices, particularly for operation in the multiplexing mode. The cyanophenyl esters may be used in a wide variety of compositions. The compounds are stable, inert to moisture, light and oxygen and have low viscosity. Moreover, they can be used in compositions using the guest-host effect.

25 Claims, 10 Drawing Figures

LIQUID CRYSTAL COMPOUND AND COMPOSITIONS CONTAINING SAME

This is a continuation of application Ser. No. 46,583, filed June 7, 1979, now abandoned.

BACKGROUND OF THE INVENTION

The present invention relates to a new type of organic compound which in a number of its embodiments has a positive dielectric anisotropy and which presents a stable liquid crystal state over a wide temperature range. It can be used for a twisted nematic liquid crystal display device of the more common types as well as for those employing the guest-host effect. For a long life, it is necessary that the liquid crystal compound be stable against attack by external factors such as water, air, light and the like. Furthermore, it is necessary that the compositions utilizing liquid crystal display devices remain in the nematic state over a wide temperature range, generally it being necessary that the nematic state temperature range include room temperature. Also, the material should be colorless in addition to being chemically stable.

The compounds of the present invention possess the requisite properties making them suitable for use in liquid crystal display devices whether of the more common type or involving the guest-host effect or multiplexing.

SUMMARY OF THE INVENTION

Substituted phenyl esters of substituted cyclohexyl carboxylic acid are liquid crystal compounds useful in liquid crystal display devices, and particularly in those where multiplexing is to be used or the guest-host effect is to be used. These compounds may be described in terms of two general formulas, these being

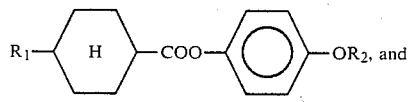

(I)

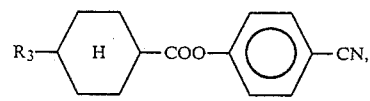

(II)

where $R_1$, $R_2$, and $R_3$ represent an n-alkyl group having one to six carbon atoms. Type I and II compounds may be used together and may be used in combination with either or both of the following types of compounds:

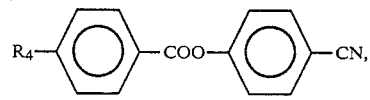

(III)

where $R_4$ represents an n-alkyl group having one to five carbon atoms, and

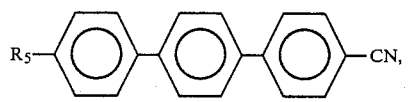

(IV)

where $R_5$ represents an n-alkyl group having three to eight carbon atoms.

The compounds disclosed above may be used in display devices wherein a pair of opposed electrode substrates have a seal therebetween for hermetically sealing compositions containing such compounds therein.

Type I and II compounds may be synthesized by reducing the corresponding substituted benzoic acid to the cyclohexyl carboxylic acid, converting same to the acid chloride with thionyl chloride and reacting the acid chloride with the corresponding substituted phenol. The condensation with the phenol is carried out in a dry solvent containing an appropriate base, preferably an amine.

Accordingly, an object of the present invention is a group of compounds suitable for use in liquid crystal display devices.

A further object of the present invention is a group of compositions incorporating said compounds.

A further object of the present invention is a method of synthesizing compounds in said group.

Yet another object of the present invention is a liquid crystal display device incorporating said compounds, said compounds being particularly suitable for use in liquid crystal display devices operating in the multiplex mode or utilizing the guest-host effect.

An important object of the invention is a group of compounds which are liquid crystal materials and which are stable to chemical reagents, light and heat.

Still other objects and advantages of the invention will in part be obvious and will in part be apparent from the specification.

The invention accordingly comprises the several steps and the relationship of one or more of such steps with respect to each of the others, and the composition possessing the features, properties and the relationship of constituents which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings in which.

DESCRIPTION OF THE PREFERRED EMBODIMENTS

Figure 1:
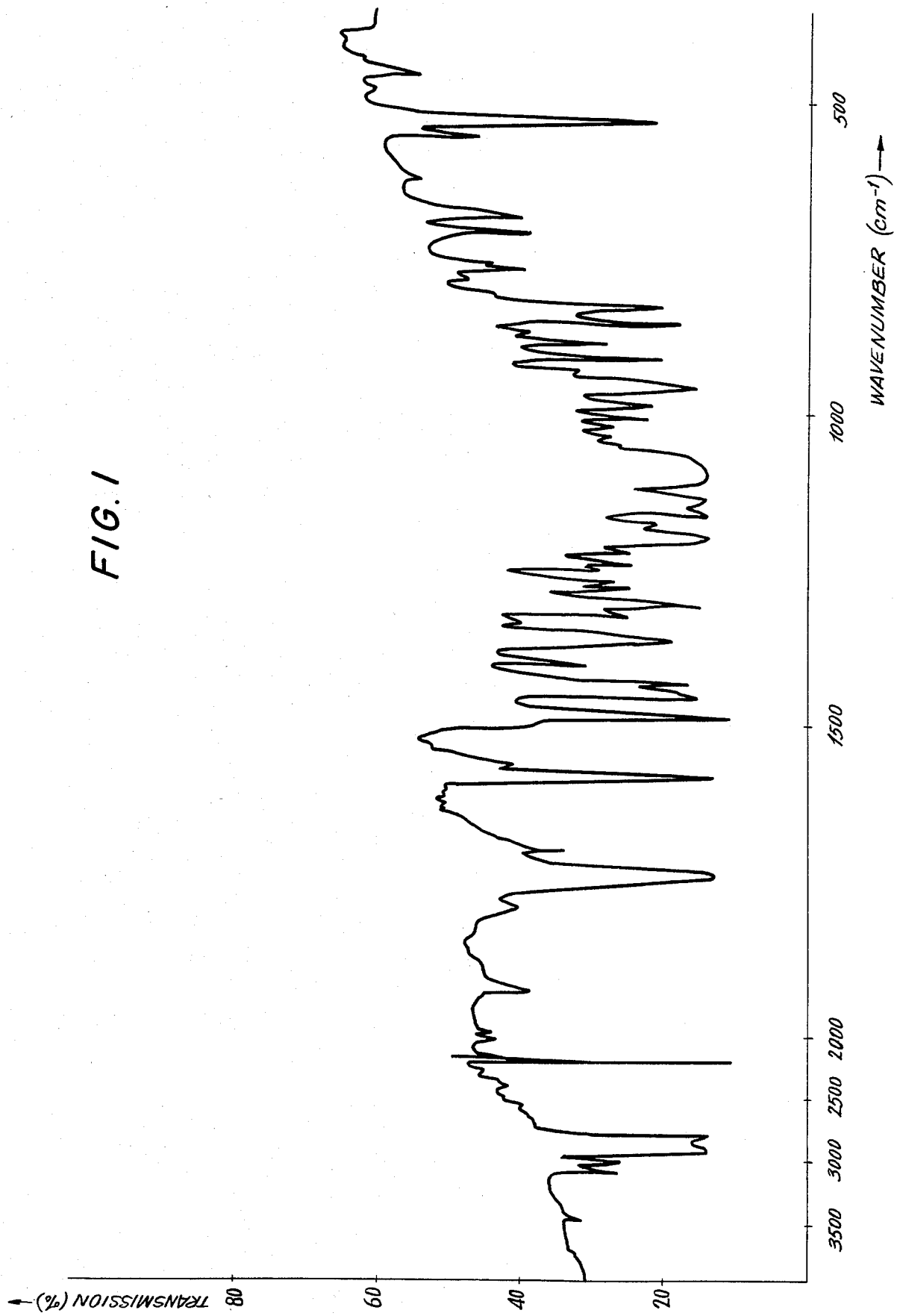
FIGS. 1-6 show infrared absorption spectra of compounds in accordance with the present invention.

Compounds in accordance with the present invention may be represented by the following general formulas,

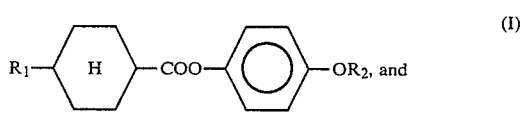

(I)

-continued

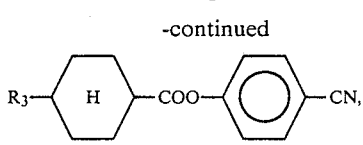

where $R_1$, $R_2$, and $R_3$ represent an n-alkyl group having one to six carbon atoms.

To synthesize

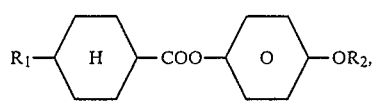

the substituted benzoic acid,

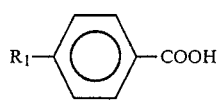

is first reduced to the cyclohexyl carboxylic acid. Reduction is preferably carried out in an autoclave at elevated temperature and pressure by procedures well-known to those skilled in the arts. A catalyst may be employed, if desired. The cyclohexyl carboxylic acid is then converted to the corresponding acid chloride, preferably through the use of thionyl chloride. After conversion to the acid chloride, excess thionyl chloride is removed by distillation. The substituted phenol to be condensed with the acid chloride is dissolved in dry ethyl ether containing a base, preferably triethylamine. The addition is carried out over an ice bath. After completion of the addition, the mixture is refluxed over a water bath. At the completion of the condensation, the ethyl ether is removed by distillation and the residue is recrystalized from a mixture of ethanol and normal hexane. The yield ranges from 20 to 50 percent. The reaction can be used for preparation of either the Type I or the Type II compounds, it being necessary only to use the appropriate substituted phenol. Following are examples of syntheses of various embodiments of the invention.

EMBODIMENT 1

Production of the 4-(n-hexyl)-cyclohexyl carboxylic acid-4'cyanophenylester. 10.6 g of 4-(n-hexyl)-cyclohexyl carboxylic acid, obtained from the reduction of 4-(n-hexyl)benzoic acid, are mixed with 12 g of thionyl chloride in a 100 ml flask and refluxed until the evolution of gas stops. The mixture is allowed to rest for about an hour after which the excess thionyl chloride is removed by distillation under reduced pressure. The 4-(n-hexyl)-cyclohexyl carboxylic acid chloride obtained thereby is redistilled at reduced pressure (0.1 mmHg, 103° C. to 106° C.), obtaining 9.3 g.

Next, 5 g of p-cyanophenol are dissolved in 80 ml of dehydrated ethyl ether, in an elongated flask, and 10 g of triethylamine are added thereto and the solution is cooled with ice. To this solution are added the 4-(n-hexyl)-cyclohexyl carboxylic acid chloride dissolved in 20 ml of ethyl ether, the addition being carried out gradually. As the reaction proceeds, the hydrochloric acid salt of the triethylamine is produced. The reaction mixture is refluxed in a water bath for about an hour to complete the reaction. The system is cooled, the salt is hydrolyzed and the ethyl ether solution is washed three times in 5N hydrochloric acid, three times with 10% aqueous sodium hydroxide and three times with water, after which it is dried using anhydrous sodium sulfate. The sodium sulfate is filtered off and the ethyl ether is removed by distillation. Finally, the residue is recrystallized repeatedly from a solution of ethanol and normal-hexane, producing a yield of 4 g of colorless, needle-shaped crystals. The yield is 27%.

The resulting compound, namely, the 4-(n-hexyl)-cyclohexyl carboxylic acid-4'-cyanophenylester has a melting point of 49° C. and a clearing point of 71° C. The infrared absorption spectrum of the compound is shown in FIG. 1. The enthalpy of fusion, ΔH obtained by D.T.A. was 11.3 Kcal.

EMBODIMENTS 2–6

Embodiments 2–6 were prepared by the same method as was embodiment 1, the only difference being that corresponding benzoic acids and substituted phenyls were selected to yield the desired final products. Table 1 shows the yield of the acid chlorides as prepared from the various substituted benzoic acids and the boiling points thereof and Table 2 shows the yield and properties of the final products obtained from the corresponding acid chlorides.

TABLE 1

| | R | Amount of R-substituted carboxylic acid used | Acid chloride Compound | | | |
|---|---|---|---|---|---|---|
| | | | Yield (g) | Yield (%) | Distillation Pressure (mmHg) | Boiling point (°C.) |
| Embodiment 1 | $C_6H_{13}$ | 10.6 | 9.3 | 80.6 | 0.1 | 103~106 |
| Embodiment 2 | $C_5H_{11}$ | 9.9 | 9.0 | 83.0 | 0.5 | 82~86 |
| Embodiment 3 | $C_4H_9$ | 9.2 | 7.6 | 75.1 | 1 | 86~89 |
| Embodiment 4 | $C_3H_7$ | 8.5 | 7.5 | 79.6 | 1 | 57~59 |
| Embodiment 5 | $C_2H_5$ | 7.8 | 7.6 | 87.1 | 0.5 | 49~58 |
| Embodiment 6 | $CH_3$ | 7.1 | 6.8 | 84.8 | 88 | 125~128 |

TABLE 2

Figure 2:
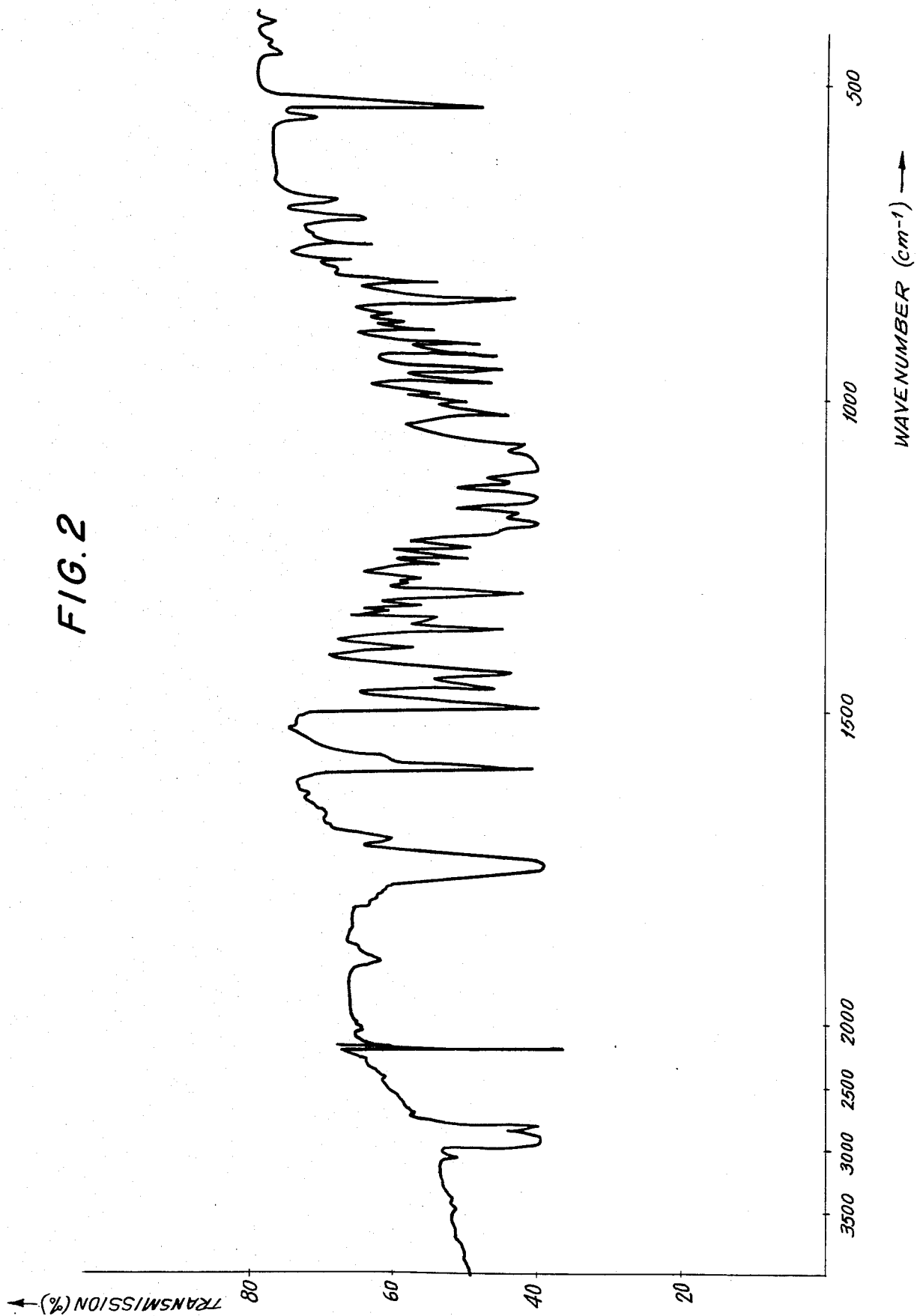

| | R | Amount of acid chloride compound used | Product | | | | | |
|---|---|---|---|---|---|---|---|---|
| | | | Yield (g) | Yield (%) | Melting point (°C.) | N-I point (°C.) | ΔH (Kcal) | Infrared absorption spectrum |
| Embodiment 1 | $C_6H_{13}$ | 6.9 | 2.5 | 26.6 | 49 | 71 | 11.3 | FIG. 1 |
| Embodiment 2 | $C_5H_{11}$ | 6.5 | 4.1 | 45.6 | 46.5 | 77.5 | 8.5 | FIG. 2 |

TABLE 2-continued

Figure 3:
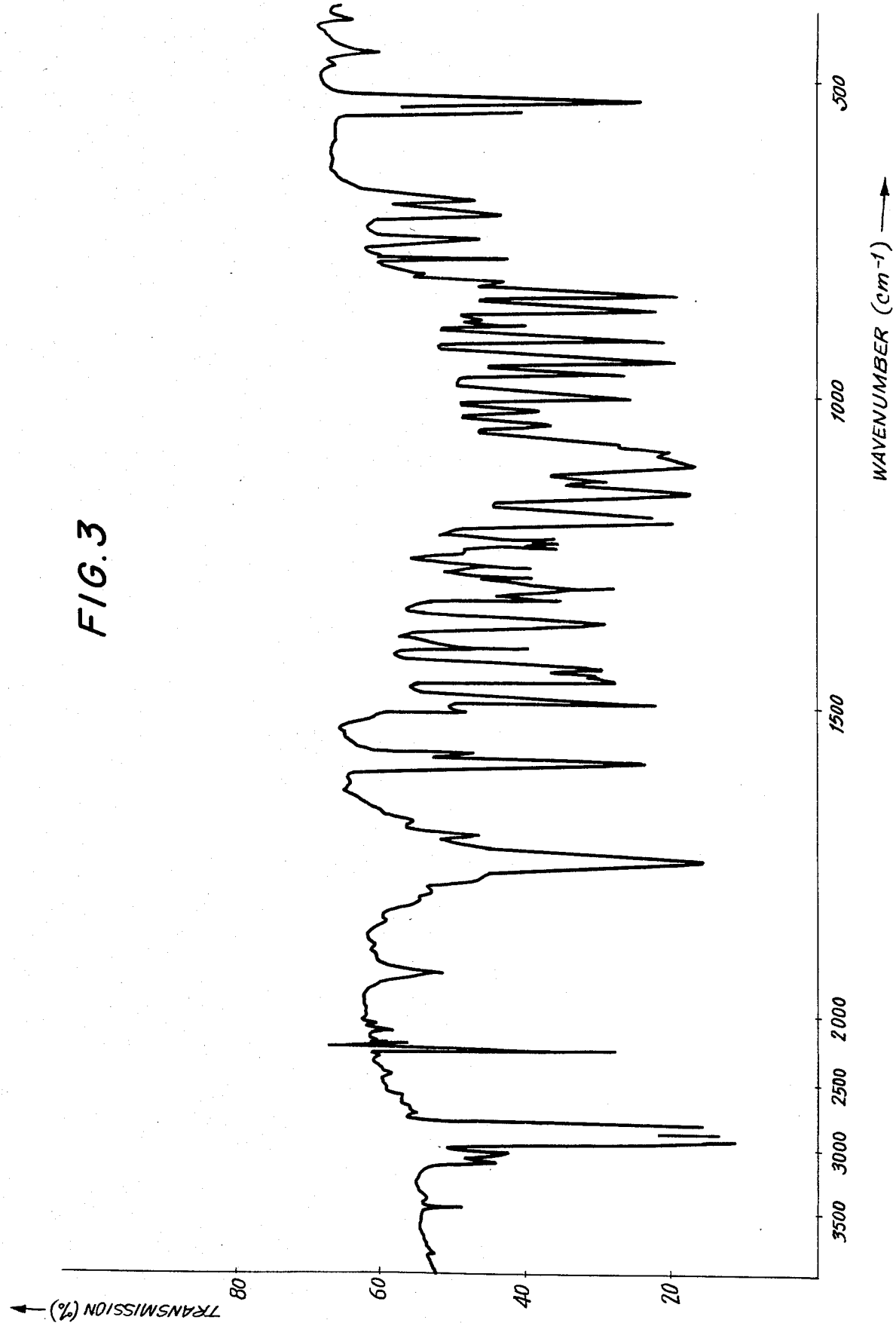
Figure 4:
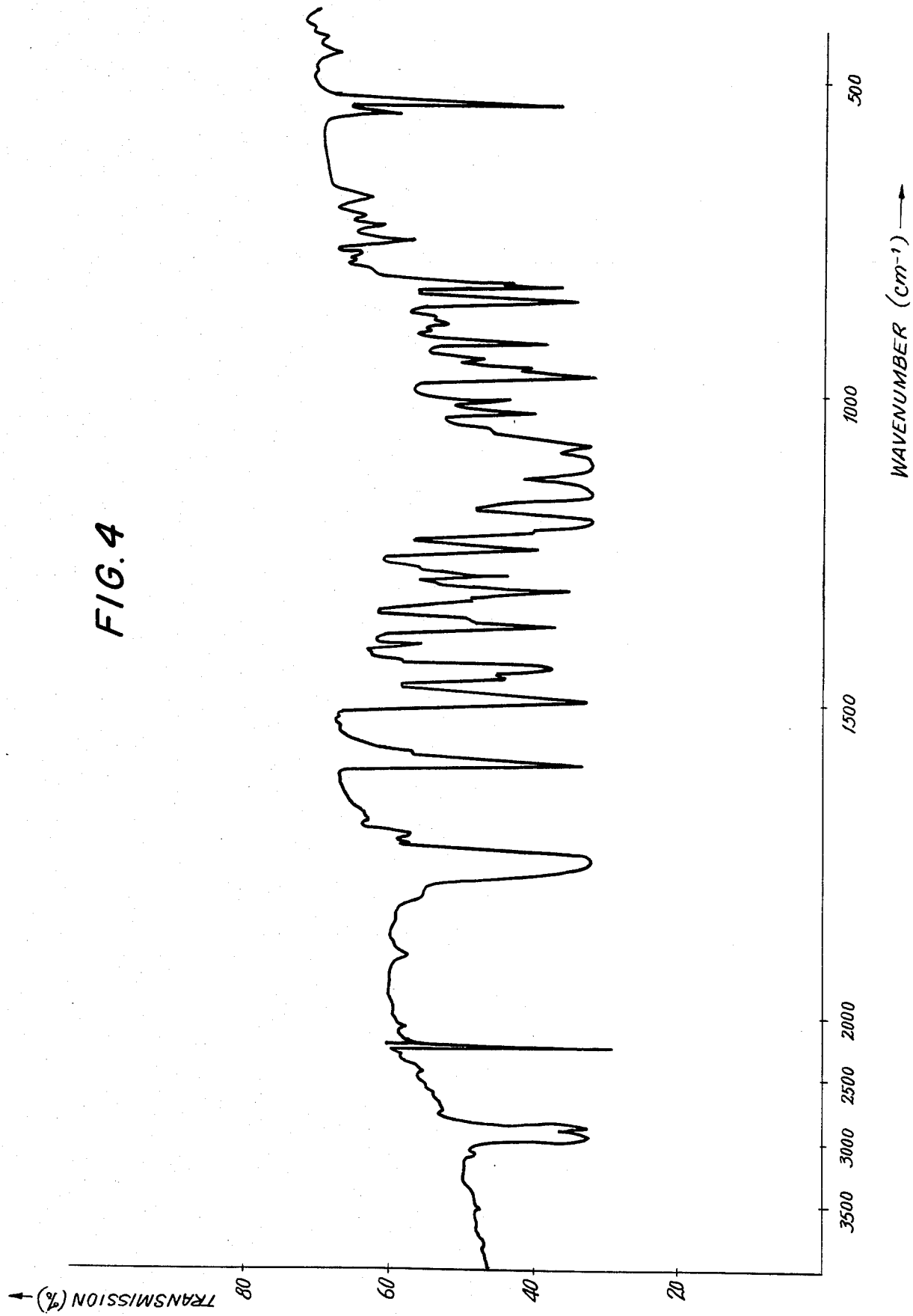
Figure 5:
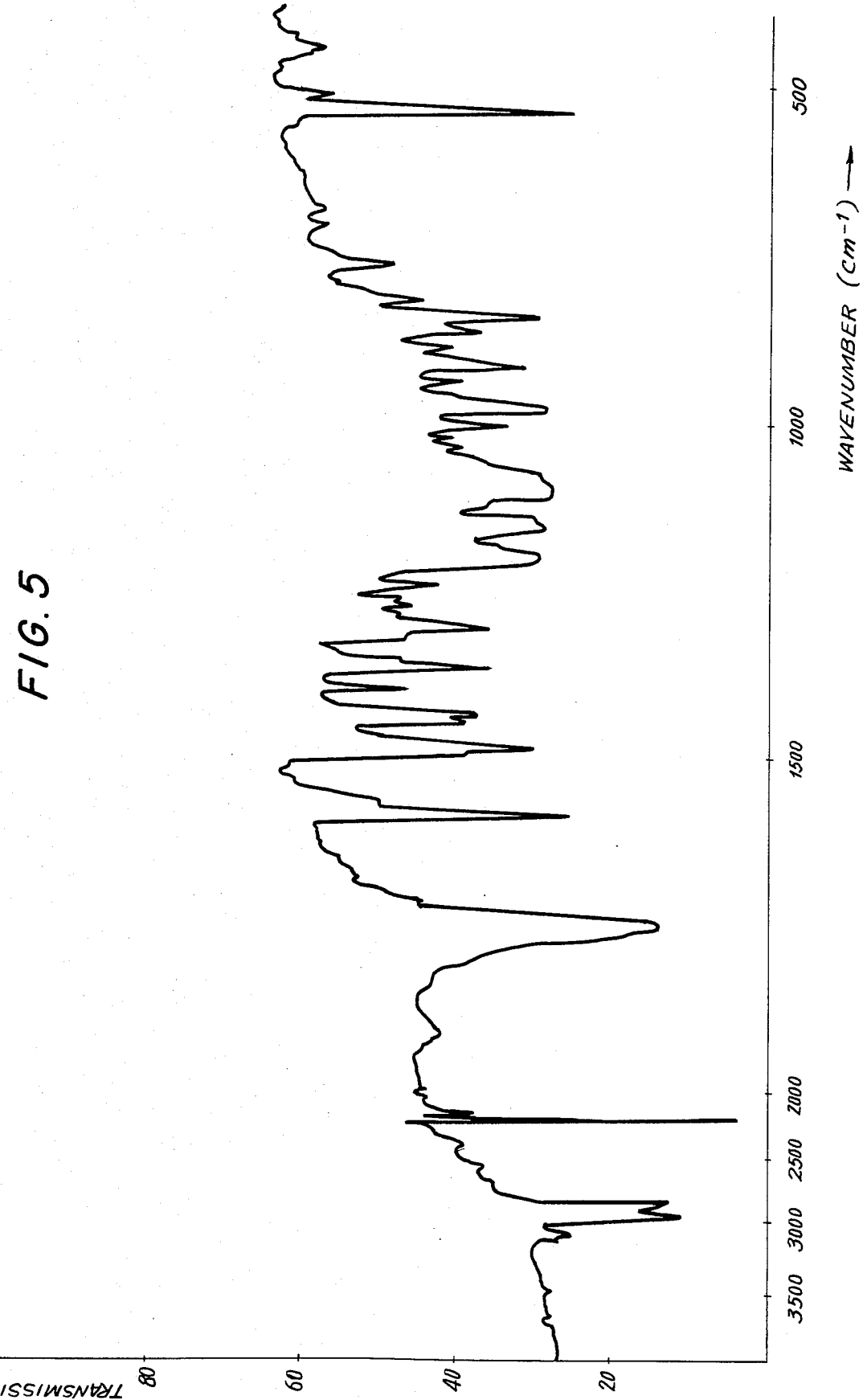
Figure 6:
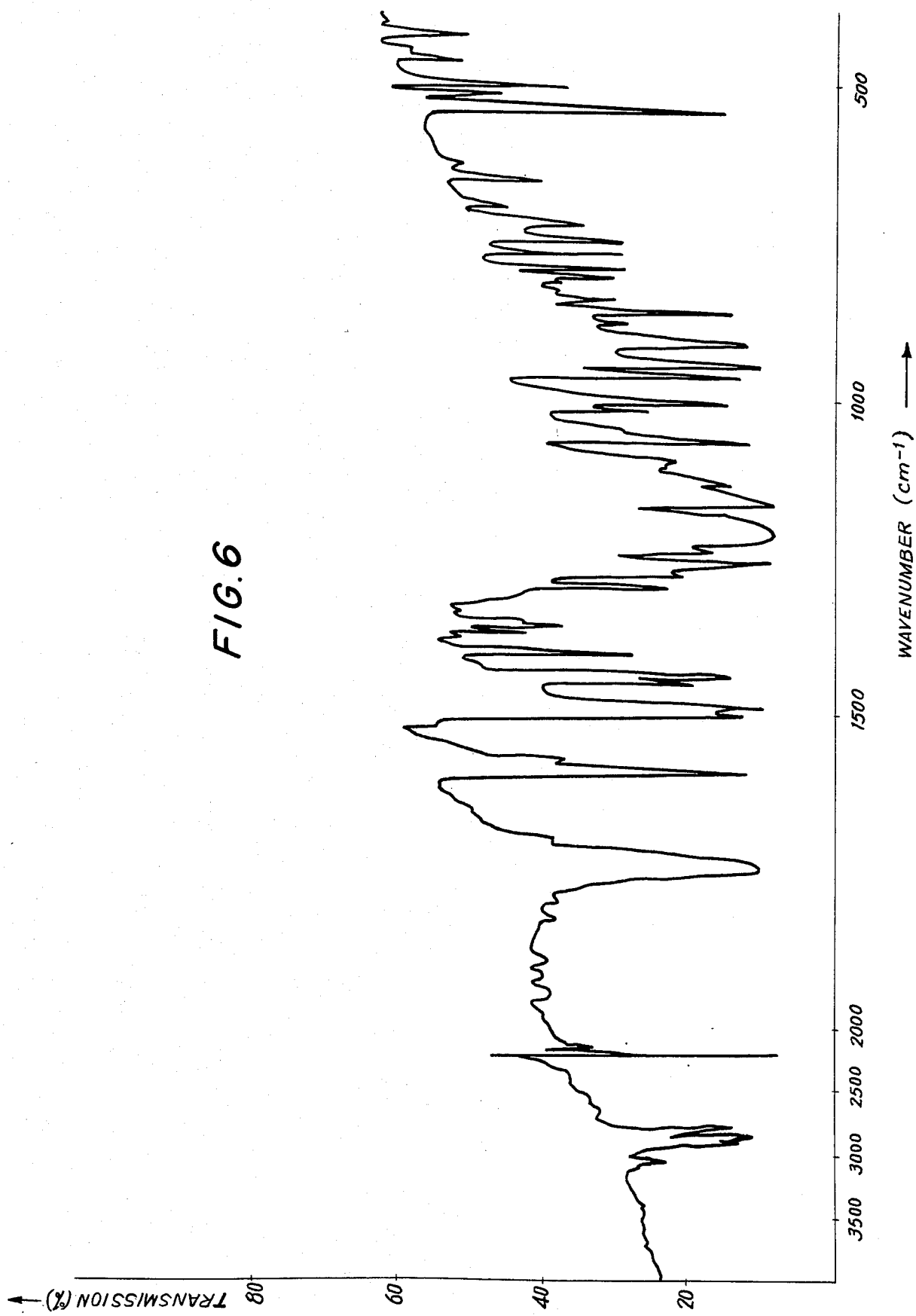

| | R | Amount of acid chloride compound used | Product Yield (g) | Yield (%) | Melting point (°C.) | N-I point (°C.) | ΔH (Kcal) | Infrared absorption spectrum |
|---|---|---|---|---|---|---|---|---|
| ment 2 | | | | | | | | |
| Embodiment 3 | C$_4$H$_9$ | 6.1 | 3.4 | 49.7 | 43 | 66.5 | 7.7 | FIG. 3 |
| Embodiment 4 | C$_3$H$_7$ | 5.7 | 2.7 | 32.6 | 54 | 68.5 | 8.09 | FIG. 4 |
| Embodiment 5 | C$_2$H$_5$ | 5.2 | 3.2 | 41.5 | 46 | 31* | 5.02 | FIG. 5 |
| Embodiment 6 | CH$_3$ | 4.8 | 4.0 | 54.8 | 63** | — | 9.0 | FIG. 6 |

*Monotropic
**No nematic phase

Compounds of Type I,

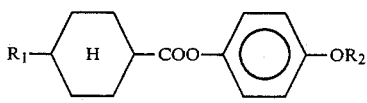

and compounds of Type II,

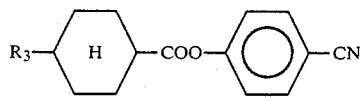

may be used alone or together with compounds of Type III,

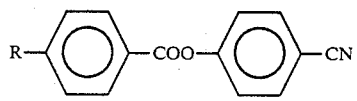

or compounds of Type IV,

again, either alone or together.

Compositions containing mixtures as aforenoted may be used in twisted nematic display devices wherein the display is effected by applying an electric field to the liquid crystal composition in the nematic crystal phase and in which the liquid crystal molecules are disposed in helices. The compositions are particularly effective for use in displays which rely upon the guest-host effect which contain a dichroic dye in the liquid crystal composition, the display being effected by applying an electric field to electrodes disposed upon electrode substrates, the liquid crystal composition being hermetically sealed between the plates. For an effective display and long life, it is essential that the composition be stable against such external factors as moisture, air, light, heat and the like, and that the composition have a liquid crystal temperature range suitable for the display and that the drive characteristics of the compositions be suitable.

The manner of the drive characteristics becomes important in view of the fact that multiplex drive systems have come into use, multiplex drive systems being desirable because the number of lead wires required is smaller than with the usual type of displays, the number of lead wires being proportional to 1/(duty ratio) in contrast with the fact that the number of lead wires for the conventional static drive systems is equal to the number of display segments.

Previously, azoxy-type liquid crystal compositions were used for multiplex driving, the general formula being,

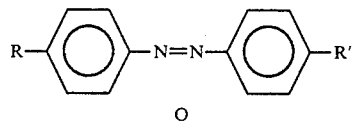

where R and R' represent an alkyl group and an alkoxy group, respectively, the alkoxy group being mixed with a biphenyl-type liquid crystal material having the general formula:

where R represents an alkyl group or an alkoxy group.

Such liquid crystal compositions have a number of faults. The azoxy type liquid crystal composition has good multiplex driving system characteristics, but it is sensitive to light so that in order to prevent deterioration of the composition a yellow filter must be used, the azoxy compound absorbing light in this range. Consequently, the display device is yellow in appearance and loss of contrast results so that the display is poor in quality.

Biphenyl-type liquid crystal compositions are stable against the various external factors and a liquid crystal display device employing these materials need not be provided with a yellow filter. Accordingly, liquid crystal display devices based on the biphenyl-type liquid crystal materials are free of color. However, they suffer from the disadvantage that the multiplex drive systems are poor so that multi-stage drive is difficult.

In a first embodiment of the present invention the liquid crystal composition includes

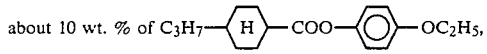

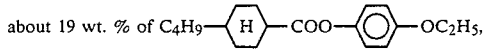

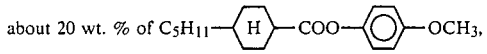

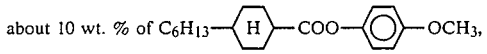

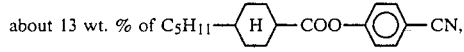

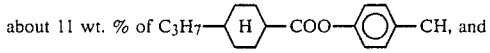

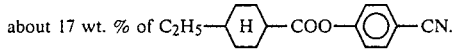

So far as the multiplex drive systems are concerned, these can be improved by about 10 to 20% by blending with appropriate components, but the result is still unsatisfactory because the viscosity increases and the low temperature characteristics are poor.

The present invention eliminates the above mentioned disadvantages, the novel liquid crystal compositions disclosed herein being stable against the various external factors, having a wide temperature range for the nematic liquid crystal phase and excellent multiplex drive sytem characteristics. These characteristics are obtained by mixing compounds of Types I, II, III and IV as exemplified in Table 3.

TABLE 3

| Embodiments | | | 1 | 2 | 3 | 4 | 5 | 6 | 7 | 8 | 9 |
|---|---|---|---|---|---|---|---|---|---|---|---|
| Com- | (I) | 1 | 11.1 | 10.2 | 9.9 | 9.4 | 7.4 | 6.7 | — | — | — |
| pounds | | 2 | 22.2 | 20.2 | 19.7 | 18.7 | 14.7 | 13.4 | 18.7 | 18.7 | 19.5 |
| (wt %) | | 3 | — | — | — | — | — | — | 19.6 | 19.6 | 20.3 |
| | | 4 | 11.9 | 11.0 | 10.7 | 10.2 | 8.0 | 7.2 | — | — | — |
| | (II) | 5 | 7.0 | 6.4 | 6.3 | 6.0 | 14.0 | 12.7 | — | — | — |
| | | 6 | 11.8 | 10.8 | 10.5 | 10.0 | 13.7 | 12.5 | 10.0 | — | — |
| | | 7 | 20.4 | 18.7 | 18.2 | 17.3 | 23.8 | 21.6 | 17.3 | 19.3 | 19.3 |
| | | 8 | 15.9 | 14.6 | 14.2 | 13.5 | 18.5 | 16.9 | 13.5 | 15.5 | 15.5 |
| | (III) | 9 | — | 8.1 | 10.6 | 9.5 | — | — | 15.4 | 19.4 | 18.0 |
| | (IV) | 10 | — | — | — | 5.4 | — | 9.0 | 5.4 | 7.4 | 7.4 |
| N-I point (°C.) | | | 64.5 | 61.5 | 60.5 | 70 | 61 | 75 | 70 | 71.5 | 72 |
| ½ duty | Center voltage | | 3.00 | 2.76 | 2.56 | 2.76 | 2.75 | 2.98 | 2.65 | 2.57 | 2.64 |
| V-2V | Margin | | 10.8 | 10.1 | 10.6 | 12.4 | 8.7 | 10.7 | 12.3 | 13.1 | 12.9 |
| ⅓ duty | Center voltage | | 3.29 | 3.02 | 2.83 | 3.02 | 3.03 | 3.25 | 2.90 | 2.81 | 2.90 |
| V-3V | Margin | | 7.3 | 6.5 | 6.6 | 8.6 | 5.3 | 6.8 | 9.2 | 10.0 | 9.7 |

The N-I point is the transition temperature from the nematic phase to the isotropic phase of the liquid crystal composition which is obtained during the mixing of the compounds in the embodiment. Each of the embodiments was allowed to remain in a twisted nematic cell in a cryostat at −10° C. for at least one month and all of the compositions maintained the nematic phase throughout the entire period.

The center voltage and the margin are defined as follows: The composition is placed in a nematic cell with a twist angle of 94° and viewed at an angle of 10° to the front perpendicular and the ON waveform is applied thereto at 0° C. and the voltage is taken at 90% transmission for a drive with ½ duty and V to 2 V and the voltage is taken at 70% transmission for a drive with ⅓ duty and V to 3 V. $V_{OFF}$ is measured when the above-mentioned cell is viewed at an angle of 40° to the front perpendicular and the OFF waveform is applied thereto at 40° C. for both cases of drive with ½ duty and V to 2 V and ⅓ duty and V to 3 V.

$$\text{Center voltage} = \frac{V_{ON} + V_{OFF}}{2} \quad (V)$$

$$\text{Margin} = \frac{1}{2} \cdot \frac{V_{OFF} - V_{ON}}{\text{center voltage}} \times 100$$

$$= \frac{V_{OFF} - V_{ON}}{V_{ON} + V_{OFF}} \times 100 \, (\%)$$

Figure 7:
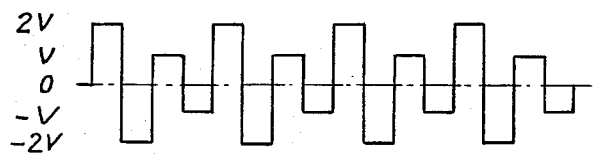
FIGS. 7-9 are driving wave forms used to measure multiplex system characteristics of a liquid crystal display device incorporating compositions in accordance with the present invention.
Figure 8:
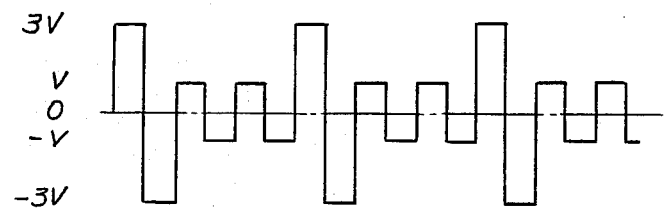
Figure 9:
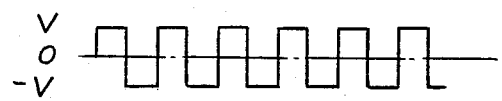

Now turning to the embodiments shown in Table III, embodiment 1 is a liquid crystal composition containing only compounds of the general formulas I and II, the content of Type II compounds being 55 weight percent, and these being the compounds with positive dielectric anisotropy. The margin is 10.8% in the case of the drive with ½ duty and V to 2 V and at 7.3% in the case of the drive with ⅓ duty and V to 3 V. Such values are quite satisfactory, considering the margin for other types of liquid crystal compositions. For an azoxy type composition, the margin is 12 to 13% when driven with ½ duty and V to 2 V and is 8 to 9% when driven with ⅓ duty and V to 3 V. For compositions of the biphenyl type, the margin is 7 to 8% when driven with ½ duty and V to 2 V and is 2 to 3% when driven with ⅓ duty and V to 3 V. The form of the driving voltages for both types of duty is shown in FIGS. 7 and 8, these as showing the $V_{ON}$ wave forms. The wave form for the OFF voltage is shown in FIG. 9.

Embodiments 2 and 3 are liquid crystal compositions which are obtained by adding the liquid crystal compound of the general formula III to a liquid crystal composition according to embodiment I. As the quantity of III compound added is increased, the center voltage decreases. In this case, the reduction of the center voltage is greater than that of the liquid crystal composition of embodiment 5 where only compounds of Types I and II are used and the compound of Type II is present to the quantity of 70 weight percent. The compound of Type III is very effective in adjusting the center voltage of compositions containing only compounds of Types I and II.

Embodiment 4 is a liquid crystal composition obtained by adding the compound of the general formula IV to the liquid crystal composition of embodiment 3. The addition of the compound of Type IV raises the center voltage only slightly; however, Type IV compound produces a pronounced raising of the margin. Moreover, it also raises the N-I point and thereby increases the temperature range over which the composition can be used. The effect of adding the Type IV compound is very substantial and can be confirmed by comparing embodiment 5 with embodiment 6, embodiment 5, like embodiments 1, 2 and 3 having no Type IV compound therein.

Embodiments 7, 8 and 9 show that a delicate voltage adjustment may be obtained without reducing the margin by controlling the compounds of Types III and IV. In these embodiments, it can be seen that satisfactory characteristics can be obtained through the use of 6 compounds. Usually about 4 or 5 different compounds are necessary for azoxy type compositions and about 7 to 10 different compounds are necessary for biphenyl type compositions.

Although the presentation of the characteristics of the compositions and compounds taught herein has been in terms of multiplex driving, the compositions and compounds also are most suitable for static drives as compared with conventional liquid crystal compositions. For instance, the fluctuation of the voltage which is necessary for the voltage at 90% transmission in the temperature range of 0° to 40° C. is 7 mV/°C. to 9 mV/°C. in the liquid crystal compositions according to the present invention, 5 mV/°C. to 7 mV/°C. for azoxy type liquid crystal type compositions and 11 mV/°C. to 13 mV/°C. for biphenyl type liquid crystal type compositions. Accordingly, the liquid crystal display means as taught herein has wide adaptability for use in various types of liquid crystal display devices, whether multiplex or static and whether or not including dichroic dyes.

Figure 10:
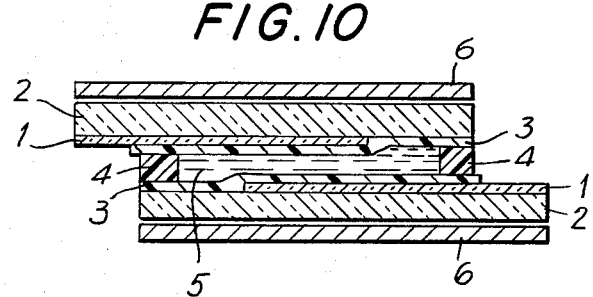
FIG. 10 is a sectional view of such a liquid crystal display device.

A twisted nematic cell in which the compounds and compositions of the present invention may be used is shown in FIG. 10, transparent electrodes 1 being disposed on the inner faces of pyrex glass base plate 2, also termed electrode substrates. A polyimide film is disposed appropriately over the substrates, the substrate being separated by a spacer 4 of polyester. Liquid crystal composition 5 is protected from contamination by the spacer and the base plates and the cell consisting of the base plates 2, the spacer 4 and the liquid crystal composition 5 therebetween, is sandwiched between polarizing plates 6.

FIGS. 1-6 show infrared spectra of the embodiments of Tables 1 and 2 numbered correspondingly. FIGS. 7-9 are the driving wave forms used in multiplexing.

It is also to be understood that the following claims are intended to cover all of the generic and specific features of the invention herein described, and all statements of the scope of the invention which, as a matter of language, might be said to fall therebetween.

What is claimed is:

1. A method of presenting a display in a liquid crystal display device, comprising the step of applying multiplex driving signals to a liquid crystal composition having a positive dielectric anisotropy in the twisted nematic field effect mode, said composition consisting essentially of about 27.3 to 59.0 weight percent of at least one liquid crystal compound having the formula

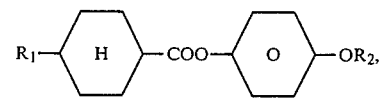

termed Type I wherein $R_1$ and $R_2$ and n-alkyl with one to six carbon atoms and about 41.0 to 72.7 weight percent of at least one liquid crystal compound having the general formula

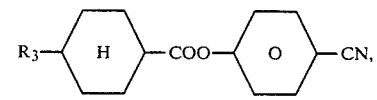

termed Type II wherein $R_3$ is n-alkyl with one to six carbon atoms, said Type I and Type II compounds included in the composition to increase the dynamic margin of the liquid crystal display device.

2. The method of presenting the display of claim 1, wherein said liquid crystal composition further comprises at least one compound from the group consisting of compounds having the general formula

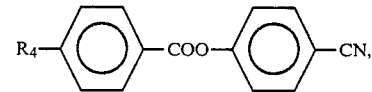

termed Type III wherein $R_4$ represents n-alkyl with one to five carbon atoms and compounds having the general formula

termed Type IV wherein $R_5$ represents n-alkyl with five to eight carbon atoms.

3. The method of presenting the display of claim 1, wherein said Type I and Type II compounds consist of the following compounds and are termed as follows:

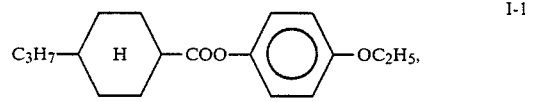

I-1

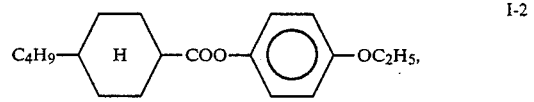

I-2

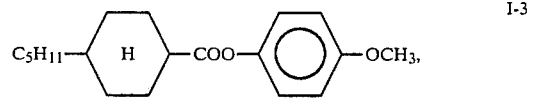

I-3

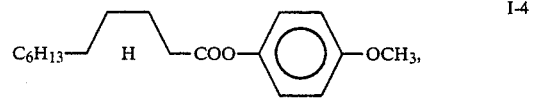

I-4

-continued

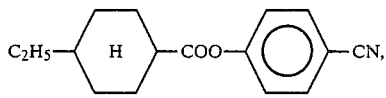 II-5

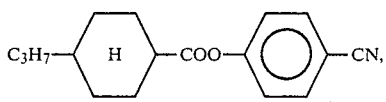 II-6

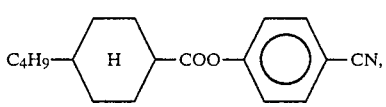 II-7

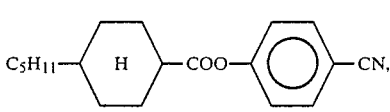 II-8.

4. The method of presenting the display of claim 1, wherein said liquid crystal composition includes about 10 weight percent of

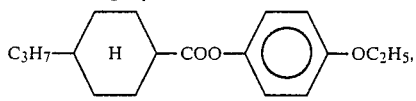

about 19 weight percent of

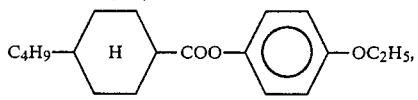

about 20 weight percent of

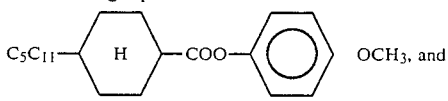 and about 10 weight percent of

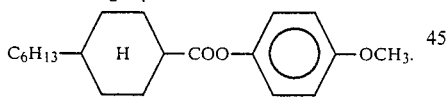

5. The method of presenting a liquid crystal display of claim 4, wherein said Type II compounds consist of about 13% n-pentyl, about 11% n-propyl, and about 17% n-ethyl cyanophenylester, all quantities being by weight.

6. The method of presenting the display of claim 3, wherein said composition consists essentially of about 11.1% I-1, 22.2% I-2, 11.9% I-4, 7.0% II-5, 11.8% II-6, 20.4% II-7 and 15.9% II-8, all quantities being by weight.

7. The method of presenting display of claim 3, wherein said composition consists essentially of about 7.4% I-1, 14.7% I-2, 8.0% I-4, 14.0% II-5, 13.7% II-6, 23.8% II-7, and 18.5% II-8, all quantities being by weight.

8. The method of presenting the display of claim 3, further including at least one compound from the group consisting of Type III compound of the formula

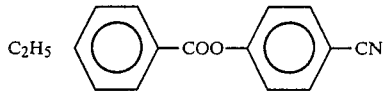

designated III-9 and a Type IV compound of the formula

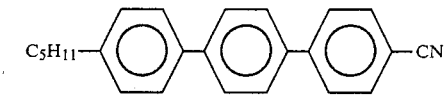

designated IV-10.

9. The method of presenting the display of claim 8, wherein said composition consists essentially of about 10.2% I-1, 20.2% II-2, 11.0% I-4, 6.4% II-5, 10.8% II-6, 18.7% II-7, 14.6% II-8 and 8.1% III-9, all quantities being by weight.

10. The method of presenting the display of claim 8, wherein said composition consists essentially of about 9.4% I-1, 18.7% I-2, 10.2% I-4, 6.0% II-5, 10.0% II-6, 17.3% II-7, 13.5% II-8, 9.5% III-9 and 5.4% IV-10, all quantities being by weight.

11. The method of presenting the display of claim 8, wherein said composition consists essentially of about 6.7% I-1, 13.4% I:2, 7.2% I-4, 12.7% II-5, 12.5% II-6, 21.6% II-7, 16.9% II-8 and 9.0% IV-10, all quantities being by weight.

12. A liquid crystal display device for displaying in a twisted nematic field effect mode comprising multiplex circuit means for generating multiplex driving signals and a liquid crystal cell including a pair of opposed substrates with electrodes selectively disposed on said substrates for receiving said signals and a liquid crystal composition sealed between said substrates, said liquid crystal composition having a positive dielectric anisotropy and consisting essentially of about 27.3 to 59.0 weight percent of at least one liquid crystal compound having the formula

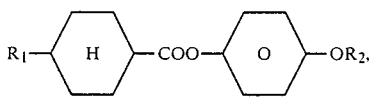

termed Type I, where $R_1$ and $R_2$ are n-alkyl with one to six carbon atoms and about 41.0 to 72.7 weight percent of at least one liquid crystal compound having the general formula

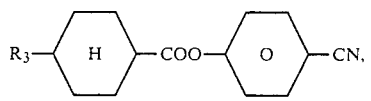

termed Type II wherein $R_3$ is n-alkyl with one to six carbon atoms, said Type I and Type II compounds included in said composition for increasing the dynamic margin of the display device said device selectively generating a display when the multiplex signals are applied to the electrode for applying a potential between opposed regions of the electrodes through said compositions for rendering the liquid crystal composition therebetween visually distinguishable from the remainder of the composition.

13. The liquid crystal display device of claim 12, wherein the liquid crystal display device further includes at least from about 8.1 to 9.5 weight percent of one compound from the group consisting of compounds having the general formula

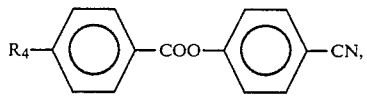

termed Type III, wherein $R_4$ represents n-alkyl with one to five carbon atoms, and from about 5.4 to 9.0 weight percent compounds having the general formula

termed Type IV wherein $R_5$ represents n-alkyl with five to eight carbon atoms.

14. The liquid crystal display device of claim 12, wherein the Type I and Type II compounds consist of the following compounds and are termed as follows:

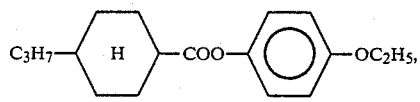
I-1

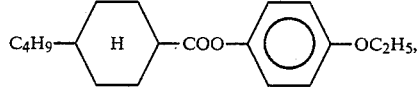
I-2

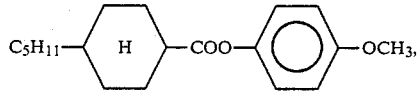
I-3

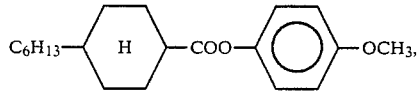
I-4

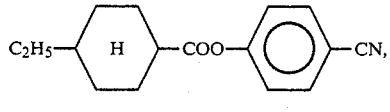
II-5

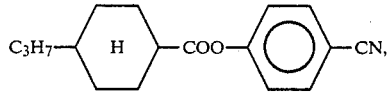
II-6

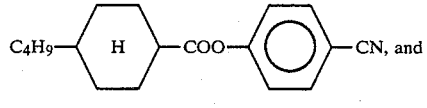
II-7;

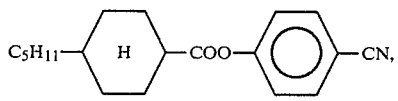
II-8.

15. The liquid crystal display device of claim 13, wherein said Type III compound is

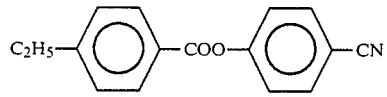

and said Type IV compound is

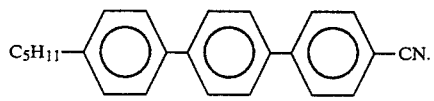

16. The liquid crystal display device of claim 12, wherein said liquid crystal composition includes about 10 weight percent of

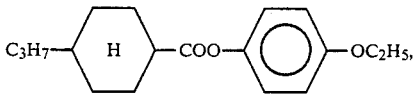

about 19 weight percent of

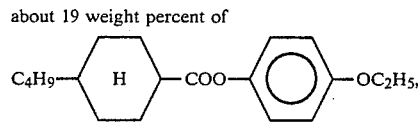

about 20 weight percent

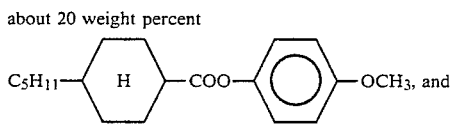

about 10 weight percent of

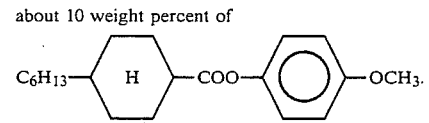

17. The liquid crystal display device of claim 16, wherein said Type II compounds consist of about 13% n-pentyl, about 11% n-propyl, and about 17% n-ethyl cyanophenylester, all quantities being by weight.

18. The liquid crystal display device of claim 14, wherein said composition consists essentially of about 11.1% I-1, 22.2% I-2, 11.9% I-4, 7.0% II-5, 11.8% II-6, 20.4% II-7 and 15.9% II-8, all quantities being by weight.

19. The liquid crystal device of claim 14, wherein said composition consists essentially of about 7.4% I-1, 14.7% I-2, 8.0% I-4, 14.0% II-5, 13.7% II-6, 23-8% II-7, and 18.5% II-8, all quantities being by weight.

20. The liquid crystal display device of claim 14, further including at least one compound from the group consisting of a Type III compound of the formula

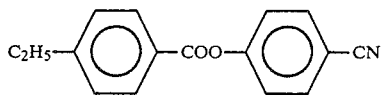

designated III-9 and a Type IV compound of the formula

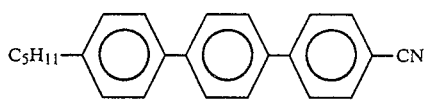

designated IV-10.

21. The liquid crystal display device of claim 20, wherein said composition consists essentially of about 10.2% I-1, 20.2% I-2, 11.0% I-4, 6.4% II-5, 10.8% II-6, 18.7% II-7, 14.6% II-8 and 8.1% III-9, all quantities being by weight.

22. The liquid crystal display device of claim 20, wherein said composition consists essentially of about 9.4% I-1, 18.7% I-2, 10.2% I-4, 6.0% II-5, 10.0% II-6, 17.3% II-7, 13.5% II-8, 9.5% III-9 and 5.4% IV-10, all quantities being by weight.

23. The liquid crystal display device of claim 20, wherein said composition consists essentially of about 6.7% I-1, 13.4% I-2, 7.2% I-4, 12.7% II-5, 12.5% II-6, 21.6% II-7, 16-9% II-8 and 9.0% IV-10, all quantities being by weight.

24. The method of presenting the display of claim 1, wherein about 45.2 weight percent of the Type I compounds and about 55.1 weight percent of the Type II compounds are present in the composition.

25. The liquid crystal display device of claim 12, wherein about 45.2 weight percent of the Type I compounds and about 55.1 weight percent of the Type II compounds are present in the composition.

* * * * *